United States Patent [19]

Schumann

[11] Patent Number: Plant 7,388

[45] Date of Patent: Dec. 4, 1990

[54] GERANIUM PLANT NAMED FISFID

[75] Inventor: Ingeborg Schumann, Hoehr-Grenzhausen, Fed. Rep. of Germany

[73] Assignee: Florfis AG, Binningen, Switzerland

[21] Appl. No.: 426,155

[22] Filed: Oct. 25, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of Geranium plant named Fisfid, particularly characterized by the combined features of salmon flower color, semi-double flower, early flowering, foliage with weak zonation, and fast rooting.

1 Drawing Sheet

The present invention comprises a new and distinct cultivar of Geranium, botanically known as *Pelargonium zonale,* and hereinafter referred to by the cultivar name Fisfid.

Fisfid is a product of a planned breeding program which has the objective of creating new geranium cultivars with salmon color, semi-double flowers, good chlorophyll quality and good growth habits.

Fisfid was originated from a hybridization made by the inventor in a controlled breeding program in Galdar, Gran Canaria, Spain, in 1983.

The female parent was Tany, an old English variety with light salmon semi-double flowers but with an inferior branching habit.

The male parent of Fisfid was Achspen×inbred line No. 1432, with Achspen having salmon semi-double flowers, leaves without zonation, and very compact growth.

Fisfid was discovered and selected as one flowering plant within the progeny of the stated cross by Ingeborg Schumann in May 1984 in a controlled environment in Hillscheid, Federal Republic of Germany.

The first act of asexual reproduction of Fisfid was accomplished when vegetative cuttings were taken from the initial selection in Spring 1985 in a controlled environment in Hillscheid, Federal Republic of Germany by, or under the supervision of, Ingeborg Schumann.

Horticultural examination of selected units initiated in February 1985 and continuing thereafter has demonstrated that the combination of characteristics as herein disclosed for Fisfid are firmly fixed and are retained through successive generations of asexual reproduction.

Fisfid has not been observed under all possible environmental conditions. The phenotype may vary significantly with variations in environment such as temperature, light intensity and daylength.

The following observations, measurements and comparisons describe plants grown in Hillscheid, Federal Republic of Germany, under greenhouse and outdoor conditions which approximate those generally used in commercial practice.

The following traits have been repeatedly observed and are determined to be basic characteristics of Fisfid, which, in combination, distinguish this Geranium as a new and distinct cultivar:

1. Salmon-rose flower color.
2. Semi-double flower form.

3. Early spring flowering.
4. Medium green leaves with weak zonation.
5. Good chlorophyll quality.

Of the many commercial cultivars known to the present inventor, the most similar in comparison to Fisfid are the cultivars Fidelio (disclosed in U.S. Plant Pat. No. 5,752) and Schoene Helena (disclosed in U.S. Plant Pat. No. 5,374), both of which have salmon rose colored flowers. Reference is made to attached Chart A which compares certain characteristics of Fisfid to those same characteristics of Fidelio and Schoene Helena. In general comparison to Fidelio and Schoene Helena, Fisfid had a somewhat greater umbel diameter and peduncle length, and a different flower color. In other respects, as will be noted in the chart, the characteristics of Fisfid are intermediate the same characteristics of the comparison cultivar. Thus, the new cultivar Fisfid is unique in several respects.

The accompanying color photographic drawing shows typical flower and foliage characteristics of Fisfid, with the colors being as true as possible with illustrations of this type.

In the following description color references are made to The Royal Horticultural Society Colour Chart (RHS). The color values were determined between 3:00 p:m. and 4:00 p.m. indoors on May 10, 1988 under 40,000 Lux light intensity at Hillscheid, Federal Republic of Germany.

Classification:

*Botanical.*—A hybrid of the genus *Pelargonium zonal* l'hert. cv Fisfid.

*Commercial.*—Zonal Geranium.

INFLORESCENCE

A. Umbel:

*Average diameter.*—Indoor, 10.9 cm; Outdoor, 10.9 cm.

*Average depth.*—Indoor, 5.4 cm; Outdoor, 4.8 cm.

*Peduncle length.*—Indoor, 15.5 cm; Outdoor, 13.0 cm.

*Pedicel length.*—Indoor, 2.7 cm; Outdoor, 2.7 cm.

B. Corolla:

*Average diameter.*—Indoor, 4.3 cm; Outdoor, 4.2 cm.

*Form.*—Semi-double.

*Color (general tonality from a distance of three meters).*—48D (the tone is lighter due to the combined effect of the main rose color and the light margins).

*Color (upper petal).*—Margin: 47C. Middle: 47C. Lower side: 41D.

*Color (lower petal).*—Margin: 47D. Middle: 47C. Lower side: 41D.

*Color (inner petal).*—Upper surface: 41C.

C. Bud:

*Shape.*—Elliptic, round.

*Color.*—Light green.

D. Reproductive organs:

*Androecium.*—8 anthers.

*Gynoecium.*—5 lobed stigma.

E. Spring flowering response period: In Hillscheid, Federal Republic of Germany in 1988, 65% of plants with at least 1 flower opened 11 weeks after planting of unrooted cuttings in week 6.

F. Outdoor flower production: The flower count in 1988 in Hillscheid, Federal Republic of Germany indicated between 50 and 55 flowers per plant for June through October observation period.

G. Durability: Medium rain resistance.

PLANT

A. Foliage:

*Form.*—Kidney shape.

*Margin.*—Bicrenate.

*Color.*—Medium green.

*Zonation.*—Weak brown zonation.

*Tolerance to botrytis.*—Medium to good.

B. General appearance and form:

*Internode length.*—Short.

*Branching pattern.*—5.0 branches per plant after 13 weeks of growing time from unrooted cuttings.

*Height.*—24 cm on average.

CHART A

COMPARISON OF FISFID, FIDELIO AND SCHOENE HELENA (measurements in centimeters)

| | FIDELIO | FISFID | SCHOENE HELENA |
|---|---|---|---|
| Color of flower | salmon rose | salmon rose with little white | salmon rose with white |
| Zone on leaves | — | weak | weak-medium |
| Branching habit (number of branches) | 5.3 | 5.0 | 4.7 |
| Number of umbels per year | 70–75 | 50–55 | 50–55 |
| Diameter of umbels indoor | 8.7 | 10.9 | 10.5 |
| Diameter of umbels outdoor | 8.3 | 10.9 | 9.7 |
| Peduncles, indoor | 14.0 | 15.5 | 14.8 |
| Peduncles, outdoor | 11.9 | 13.0 | 12.2 |
| Pedicels, indoor | 2.3 | 2.7 | 2.7 |
| Pedicels, outdoor | 2.1 | 2.7 | 2.7 |
| Corolla diameter, indoor | 5.0 | 4.3 | 4.1 |
| Corolla diameter, outdoor | 4.4 | 4.2 | 4.0 |
| Beginning of flowering 1988 (% flowering plants in 17th week) | 90% | 65% | 25% |

I claim:

1. A new and distinct cultivar of Geranium plant named Fisfid, as illustrated and described.

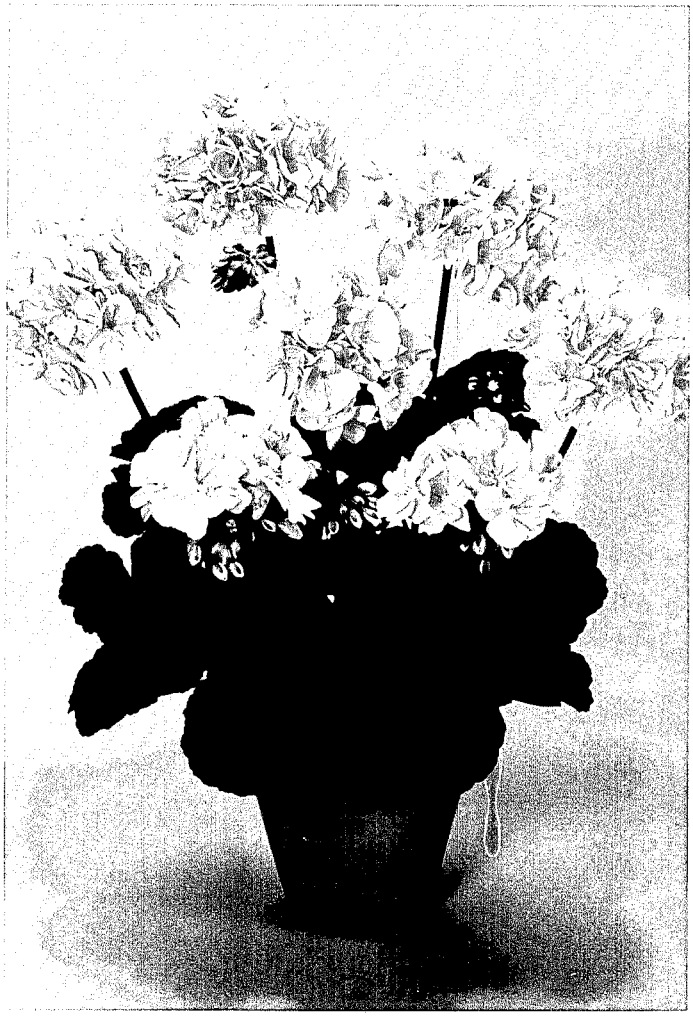

* * * * *